(12) United States Patent
Weyl et al.

(10) Patent No.: US 7,258,770 B2
(45) Date of Patent: Aug. 21, 2007

(54) GAS SENSOR

(75) Inventors: Helmut Weyl, Schwieberdingen (DE); Claudio De La Prieta, Stuttgart (DE); Andreas Hachtel, Leinfelden-Echterdingen (DE); Thomas Schulte, Stuttgart (DE); Thomas Egner, Anderson, SC (US); Juergen Wilde, Fellbach (DE); Markus Siebert, Leonberg (DE); Michael Kupzig, Niederkassel (DE); Uwe Glanz, Asperg (DE); Rainer Mueller, Stuttgart (DE); Leonore Schwegler, Stuttgart (DE); Petra Kuschel, Leonberg-Hoefingen (DE); Andreas Pesch, Krefeld (DE)

(73) Assignee: Robert Bosch GmbH, Stuttgart (DE)

( * ) Notice: Subject to any disclaimer, the term of this patent is extended or adjusted under 35 U.S.C. 154(b) by 701 days.

(21) Appl. No.: 10/444,759

(22) Filed: May 23, 2003

(65) Prior Publication Data

US 2004/0040843 A1 Mar. 4, 2004

(30) Foreign Application Priority Data

May 23, 2002 (DE) ................. 102 22 789

(51) Int. Cl.
*G01N 27/407* (2006.01)
(52) U.S. Cl. ...................... 204/424; 277/650
(58) Field of Classification Search .............. 204/424, 204/426, 428; 277/650, 653, 591
See application file for complete search history.

(56) References Cited

U.S. PATENT DOCUMENTS

| | | | |
|---|---|---|---|
| 5,467,636 A | 11/1995 | Thompson et al. | |
| 5,755,941 A * | 5/1998 | Weyl | ............ 204/424 |
| 5,846,391 A | 12/1998 | Friese et al. | |
| 6,206,377 B1 * | 3/2001 | Weyl | ............ 277/317 |
| 6,474,655 B1 | 11/2002 | Weyl et al. | |
| 2003/0015020 A1 | 1/2003 | Geier et al. | |

FOREIGN PATENT DOCUMENTS

DE 41 26 378 4/1992

(Continued)

OTHER PUBLICATIONS

J. Brandt et al., "Processing of Mullite-Based Long-Fibre Composites Via Slurry Routes and by Oxidation of an Al-Si Alloy Powder," Journal of the European Ceramic Society, 16 (1996), pp. 261-267.

(Continued)

*Primary Examiner*—Kaj K. Olsen
(74) *Attorney, Agent, or Firm*—Kenyon & Kenyon LLP (57) ABSTRACT

A gas sensor is for determining at least one physical quantity of a gas, e.g., an exhaust gas of an internal combustion engine, the gas sensor having a sensor element that is fixed in a housing of the gas sensor by a seal assembly. The seal assembly includes a sealing element, which has a ceramic and/or a metallic material. After the heat treatment, the sealing element has a maximum decrease in volume of 5 percent, or an increase in volume, based on the volume of the sealing element prior to the heat treatment.

25 Claims, 4 Drawing Sheets

FOREIGN PATENT DOCUMENTS

| | | |
|---|---|---|
| DE | 195 32 090 | 3/1997 |
| DE | 198 52 674 | 5/2000 |
| DE | 101 23 168 | 11/2002 |
| EP | 0 706 046 | 4/1996 |

OTHER PUBLICATIONS

N. Claussen et al., "Low-Shrinkage Reaction-Bonded Alumina," Journal of the European Ceramic Society, 5 (1989), pp. 29-35.

G. S. Grader et al., "Novel Ceramic Foams From Crystals of $AlCl_3(pr^i_2O)$ Complex," Journal of Materials Research, vol. 14. No. 4, Apr. 1999, pp. 1485-1949.

C. Koerner et al., "Processing of Metal Foams—Challenges and Opportunities," Advanced Engineering Materials 2000, 2, No. 4, pp. 159-191.

* cited by examiner

GAS SENSOR

CROSS-REFERENCE TO RELATED APPLICATIONS

The present application claims priority to Application No. 102 22 789.6, filed in the Federal Republic of Germany on May 23, 2002, which is expressly incorporated herein in its entirety by reference thereto.

FIELD OF THE INVENTION

The present invention relates to a gas sensor, e.g., for determining at least one physical quantity of a gas, such as an exhaust gas of an internal combustion engine, as well as a method for producing the gas sensor.

BACKGROUND INFORMATION

A gas sensor is described in German Published Patent Application No. 41 26 378. The gas sensor contains an oblong, planar sensor element, which makes contact with the gas to be analyzed, using a section on the side of the gas to be analyzed. Contact surfaces for contacting the sensor element to evaluation electronics arranged outside of the gas sensor are provided on a terminal-side section of the sensor element facing away from the section on the side of the gas to be analyzed. The measuring-gas-side and terminal-side sections of the sensor element are separated by a seal arrangement. The seal assembly is arranged between a molded ceramic part on the side of the measuring gas and a molded ceramic part on the side of the terminal. The molded ceramic parts and the seal assembly contain openings for accommodating the sensor element. To produce the seal, a premolded sealing ring is initially pressed between the two molded ceramic parts. While the sealing ring is pressed, it is converted to steatite powder, which then rests radially against the sensor element and the housing and thereby seals the sensor element in the housing. A seal assembly is also described in German Published Patent Application No. 195 32 090, where a further boron-nitride sealing element is pressed between two steatite sealing elements. As in German Published Patent Application No. 41 26 378, the sealing action may be attained in that a force is exerted by the molded ceramic parts on the sealing material in such a manner, that the sealing material is markedly compressed and presses against the sensor element and the housing due to deformation.

In the case of the described seal assemblies, it may be undesired that the sealing material is required to be under constant high pressure to achieve the required sealing effect. Therefore, such seal assemblies may be expensive and difficult to produce. In addition, the sensor element may be damaged by the forces occurring while the seal assembly is being pressed.

European Published Patent Application No. 0 706 046 describes a seal assembly, in which the sensor element is fixed in position in a ceramic retaining body by a glass seal. In addition, German Published Patent Application No. 198 52 674 and German Published Patent Application No. 101 23 168 describe a seal assembly having a sealing element, which contains a mixture of a ceramic powder, e.g. steatite, and a glass powder. The sealing element is heated to a maximum temperature of 1000 degrees Celsius. Due to this heat treatment, the glass powder is melted in the steatite matrix and thus diffuses into the pores of the steatite matrix. The ceramic portion is not sintered by the heat treatment.

In the case of seal assemblies that contain a glass fraction, it may be undesired that states of stress, which may lead to tears in the glass-containing seal, may occur during operational heating or cooling of the seal assembly, or under stress due to thermal shock. In addition, the electrical resistance of a glass-containing seal decreases considerably in response to higher temperatures occurring during the operation of the gas sensor so that unwanted currents may occur between the sensor element and the housing.

SUMMARY

An example embodiment of a gas sensor of the present invention, as well as an example embodiment of a method of the present invention for manufacturing a gas sensor, may allow a sensor element to be sealed and supported in a housing of the gas sensor in a simple manner from the standpoint of production engineering.

The seal assembly of the gas sensor according to an example embodiment of the present invention may contain a sealing element, which is subjected to a heat treatment, the heat treatment causing the sealing element to experience a maximum increase or decrease in volume of 5 percent. This allows the sealing element to enter into a gas-tight connection with the surrounding parts of the gas sensor, e.g. the housing and the sensor element, during the heat treatment. In order to maintain the sealing action, the sealing element may be mounted in the housing without being acted upon by external forces. The sealing action and positioning of the sensor element in the housing may be achieved in a reliable manner, when the sealing element experiences an increase in volume from the heat treatment.

According to an example embodiment of the present invention, the sealing element may contain a ceramic material, which is sintered by the heat treatment. Conventional methods that at least substantially prevent or compensate for sintering shrinkage of the ceramic during heat treatment may be used to manufacture such a sealing element. Several examples of such methods are described in the Journal of the European Ceramic Society, 16 (1996), pp. 261 through 267, as well as 5, (1989), pp. 29 through 35, and in J. Mater. Res., Vol. 14, No. 4, April 1999, pp. 1485 through 1949, as well as in the documents cited in these articles.

In a further example of such a method that provides a gas-tight sealing element while at least substantially preventing sintering shrinkage, one initially starts out from a starting mixture of a powder of an Al-based alloy, e.g., an Al—Mg alloy such as AlMg5, having an Mg level of 5 wt. %, with a ceramic powder, e.g., a metallic-oxide powder such as MgO. For example, 25.00 g of AlMg5 powder having an average particle size between 1 µm and 200 µm, such as, for example, 10 µm to 50 µm, and for example, approximately 30 µm, and a standard deviation of approximately 10 µm (manufacturer: Eckart Mepura, type designation: ECKA coarse aluminum sand A5) may be used with 15.66 g of MgO powder having an average particle size of 0.5 µm to 50 µm, e.g. 4 µm, and a specific surface area of 1.2 m²/g. This mixture may be stoichiometrically combined so that, in the case of complete oxidation of the Al—Mg alloy within the scope of the subsequent reaction-sintering, a spinel of the type $MgAl_2O_4$ is formed with the magnesium oxide. The starting powders used are initially introduced into ethanol and stirred intensively there, before the ethanol is drawn off again. The powder mixture is then subjected to forming, i.e. introduced into a mold and, in this manner, formed into a green body, which is subsequently compressed, so that a green, green-body density of 45% to 55%, such as, for example, 47% to 52%, sets in. If the density falls below this green density, then the ceramic material obtained in the end may have an open porosity that is too high, and/or the metal becoming liquid in the course of the subsequent reaction-sintering partially leaks out of the green body, which may affect the gas-tightness. Subsequent to the forming, reaction-sintering in an oxidizing, gas atmosphere, e.g. air, oxygen, or another oxygen-containing atmosphere, then occurs within the scope of a heat treatment, in order to form the green body. The reaction-sintering may occur in air. A heat treatment program may provide for the green body initially being heated from room temperature to 550° C. at a heating rate of 2 K/min to 5 K/min, e.g. 3 K/min. Subsequently, it is further heated from 550° C. to 700° C. at a heating rate of 0.5 K/min to 3 K/min, e.g. 1 K/min. After 700° C. is reached, the green body is further heated to 1000° C. at a heating rate of 0.5 K/min to 3 K/min, e.g. 0.5 K/min. After the final temperature of 1000° C. is reached, the sintered body is kept there for 0 to 3 h, e.g. 2 hours, and then cooled to room temperature at a cooling rate of 10 K/min.

In the course of the reaction-sintering, the alloy-powder particles or general metallic-powder particles contained in the green body are initially oxidized on the surface, before the metal present in the interior of the surface-oxidized metallic-powder particles or the alloy present there melts in response to further increasing temperatures. Therefore, molten metal surrounded by an oxide shell is formed from the metallic-powder particles. The surface-oxidized particles having molten metal in the interior then break open in response to the temperature increasing further, so that the molten metal or the molten metal alloy leak out with the molten metal due to capillary forces and the desired wettability of the ceramic-powder particles, which, as mentioned, may be made of a metallic oxide; and the molten metal or molten metal alloy initially penetrates the oxide shell, which is not melted and forms a porous matrix acting like a sponge due to the ceramic particles used, and the molten metal or molten metal alloy then reacts with the oxide shell, so that a gas-tight matrix may be formed in the explained example. This has a spinel ($MGAl_2O_4$ in the example discussed), any unreacted, metallic residues, at least substantially closed pores at the locations of the metallic-powder particles formerly present there, and possibly residues of the ceramic-powder particles. In this respect, one may also refer to the oxidic ceramic material produced as a metal-ceramic composite material due to the metal residues or alloy residues normally still present.

In the case of the discussed reaction mechanism, the degree of oxidation of the metallic-powder particles may initially be controlled by the heat-treatment program, the choice of metal or alloy, and their particle size. In order for the molten metal to leak out or overflow as extensively and effectively into the surrounding region having the metallic oxide or the ceramic particles, it may be important for the molten metal to effectively wet the metallic-oxide powder particles, which, as explained, also results in the interior of the surface-oxidized, metallic-powder particles melted in the interior defining a normally closed pore to be formed. During the heat treatment, such as, for example, when using a suitable temperature control, the time or the temperature at which the molten metal emerges from the surface-oxidized particles may be precisely set so that the reaction of the molten metal with the ceramic-powder particles occurs inside a specific temperature range, which may be adjusted to the desired polycrystalline matrix phase, i.e. in the example, the chemical compound $MgAl_2O_4$ to be formed at least partially.

In the mentioned example of a starting mixture having the Al—Mg alloy powder as metallic-powder particles and the MgO powder as ceramic-powder particles, the initially passivating formation of the oxide shell or general ceramic shell may occur on the surface of the metallic-powder particles in the temperature range between 500° C. and 600° C., so that the alloy subsequently melts inside these surface-oxidized powder particles, i.e. inside the oxide-ceramic shell. Furthermore, the sintering atmosphere and the heating speed may be selected so that this shell initially remains intact on the other side of the melting temperature of the trapped, molten metal, as well, and thus may enclose it. As the temperature increases further during the heat treatment, both the oxide shell and the trapped, molten metal expand. Since the coefficient of thermal expansion of the molten metal is greater than that of the ceramic shell, the increasing temperature may cause the ceramic shell to experience a critical stress and break open at a specific outflow temperature, so that the molten metal inside the oxidized powder particle emerges and wets the surrounding ceramic matrix having the metallic-oxide powder particles. This outflow is aided by the mentioned, desired wetting characteristics of the matrix and capillary forces, so that the molten metal may be sucked virtually completely out of the shells into the matrix.

In addition, it should be taken into consideration that the outflow temperature may be influenced by the particle size of the metallic-powder particles, their chemical composition, and the moisture content of the sintering atmosphere. The breaking-open and the flowing-out may occur in a temperature interval of 700° C. to 900° C. that may be stipulated, such as, for example, 750° C. to 800° C. Chemical reactions, which result in the hardening and densification of the matrix, may then proceed immediately after the flowing-out. Thus, oxygen from the atmosphere may be initially available in the body that still has open pores, in order to at least partially oxidize the molten metal, so that, in the mentioned example, aluminum oxide may be primarily formed, but, in addition, mixed oxides that are already more complex, such as spinel, may be secondarily formed. These reactions are associated with a local volume expansion amid simultaneous densification of the matrix, and thus may result in the desired, foam-like, structure, which may be at least substantially, and may be completely gas-tight, and in which the places at which the molten metal was previously located are present in the form of closed pores that are completely surrounded by the newly formed matrix of oxide-ceramic material. If the above-mentioned reaction process is performed at a maximum temperature of 1000° C., a multiphase structure having a dominating fraction of $Al_2O_3$ and also MgO, spinel, and small residues of metallic Al may be formed in the example, the phase fractions varying as a function of the choice of starting composition, particle sizes in the starting mixture, heating speeds, maximum temperature, sintering atmosphere, and retention time. This being the case, this material may be a foam-like, metal-ceramic composite material. A predominant or complete conversion of the matrix to spinel may be achieved by a final temperature at or above 1300° C.

An oxide-ceramic material may be obtained, which has an oxide-ceramic matrix having closed pores embedded in it and, in some instances, metallic grain regions; the locations and sizes of the pores being substantially defined by the locations of the metallic-powder particles previously there. This material may therefore have a substantially closed porosity and may be gas-tight. The shaped body may be obtained after the reaction-sintering experiences an increase in volume of 0% to 10%, and in particular 0% to 3%, compared to the volume of the green body prior to the reaction-sintering. In this respect, a ceramic material may be formed, which may be describable as a ceramic foam having pores that are at least substantially closed.

According to a further example embodiment of the present invention, the sealing element may include a metallic component and may be porous. The foam-like structure of the sealing element may cause the sealing element to have a higher elasticity than a non-porous material. Consequently, the sealing element may rest against the surrounding parts of the gas sensor while providing a good sealing effect. Mechanical stresses, which may result from temperature changes occurring during operation (thermal shock), may be reduced by the elasticity of the sealing element. This may reduce the force exerted by the sealing element on the surrounding parts of the gas sensor, e.g. the sensor element, due to such stresses. Such metallic foams and various methods for manufacturing them are described, for example, in Advanced Engineering Materials 2000, 2, No. 4, pages 159 to 191.

A example method of the present invention for producing a gas sensor may be a simple and inexpensive method for sealing and supporting a sensor element in a housing of a gas sensor.

If the material of the sealing element is selected so that, after the heat treatment, the sealing element is integrally connected to a part of the gas sensor adjacent to the sealing element, e.g. to the sensor element or the housing, then the sensor element may be supported and sealed in the housing of the gas sensor in a secure manner.

If the sealing element has a maximum glass fraction of 20 wt. %, such as, for example, a maximum glass fraction of 10 wt. %, then the sealing element may have a lower conductivity and a lower tendency to crack.

If the sealing element has a closed porosity with a maximum pore fraction of 40 percent, or if the sealing element is non-porous, then pollutants may be effectively prevented from penetrating the sealing element. In the case of a porous sealing element, the tendency to crack in response to thermal shock and mechanical stress may also decrease. Furthermore, the elasticity of a porous sealing element may reduce forces that occur as a result of such stresses and act, for example, on the sensor element.

In an example embodiment of the present invention, the pore size of at least 90 percent of the pores may lie between 10 and 60 μm, and the average pore size may lie in the range of 20 to 40 μm. This example embodiment may achieve a high sealing action while displaying a low tendency to crack.

An example embodiment of the present invention provides for the sealing element to completely fill out a region between the sensor element and the housing. The sealing element may have two or more regions, whose ceramic and metallic fractions differ. In this context, the region of the sealing element adjacent to the metallic housing has a higher metallic fraction and/or a lower ceramic fraction than the region adjacent to the sensor element. By this arrangement, the sealing element may form a reliable connection to both the metallic housing and the ceramic sensor element during the heat treatment. In the case of a metallic fraction of more than 70 weight percent, the sealing element may additionally or alternatively be joined to the housing by welding.

In an example embodiment of the present invention, a cup-shaped, metallic, machined part is provided, whose base has a recess for accommodating the sensor element. The sealing element is provided in the region between the sensor element and the hollow cylindrical wall of the machined, metallic part. The machined, metallic part may be joined to the housing by welding. The machined, metallic part may be a partial section of the housing constructed in one piece. The starting material for the sealing element may simply be introduced into the cup-shaped, machined part having the sensor element, and subjected to the heat treatment outside the gas sensor or after being introduced into the gas sensor. In a further development of this example embodiment of the present invention, the molded, metallic part has a gap for the sensor element in the region of the recess for the sensor element, in the base of the machined, metallic part; an insulating, e.g. ceramic element being arranged in the gap. The insulating element may ensure that there is adequate insulation between the sensor element and the machined, metallic part.

A further example embodiment of the present invention provides a hollow cylindrical body, which is made out of a ceramic and/or metallic material and arranged between the sensor element and the housing. The sealing element may be provided between the body and the housing and/or between the body and the sensor element.

To provide insulation and/or improve adhesion, the sealing element and/or the housing and/or the sensor element may be covered with a layer of, e.g. ceramic material or glass.

Furthermore, an intermediate layer may be provided between the sealing element and the housing, the intermediate layer containing aluminum oxide and/or zirconium oxide and/or aluminum phosphate. In the case of a ceramic sealing element, such a layer may prevent cracks from occurring in the sealing element as a result of a reaction of the ceramic material with the metallic material of the housing during the heat treatment.

Prior to the heat treatment, the starting material of the sealing element may be introduced into the housing as a preformed element or with the aid of an injection-molding process. During the heat treatment, the starting material of the sealing element may form a continuous material connection to an adjacent part of the gas sensor, in particular to the housing or the sensor element. If the sealing element is arranged in the housing or in another metallic element during the heat treatment, then the temperatures occurring during the heat treatment may only exceed 1000 degrees Celsius for a short time, in order to prevent the housing or the metallic element from melting.

If the temperature of the heat treatment is above the temperature, to which the housing of the gas sensor is normally subjected during operation, then the heat treatment may occur in the metallic element outside the housing of the gas sensor. In this case, a material having a lower temperature stability than the material of the metallic element may be selected for the housing.

The sealing element may be introduced into the seal assembly in the form of a preformed element, or with the aid of an injection-molding process. A preformed element may be provided, when the shape of the sealing element is required to be precise and constant, due to the manufacturing method and the configuration of the seal assembly or the gas sensor. However, the injection-molding process may be a simple and effective method for introducing the sealing element into the seal assembly.

DETAILED DESCRIPTION

Figure 1:
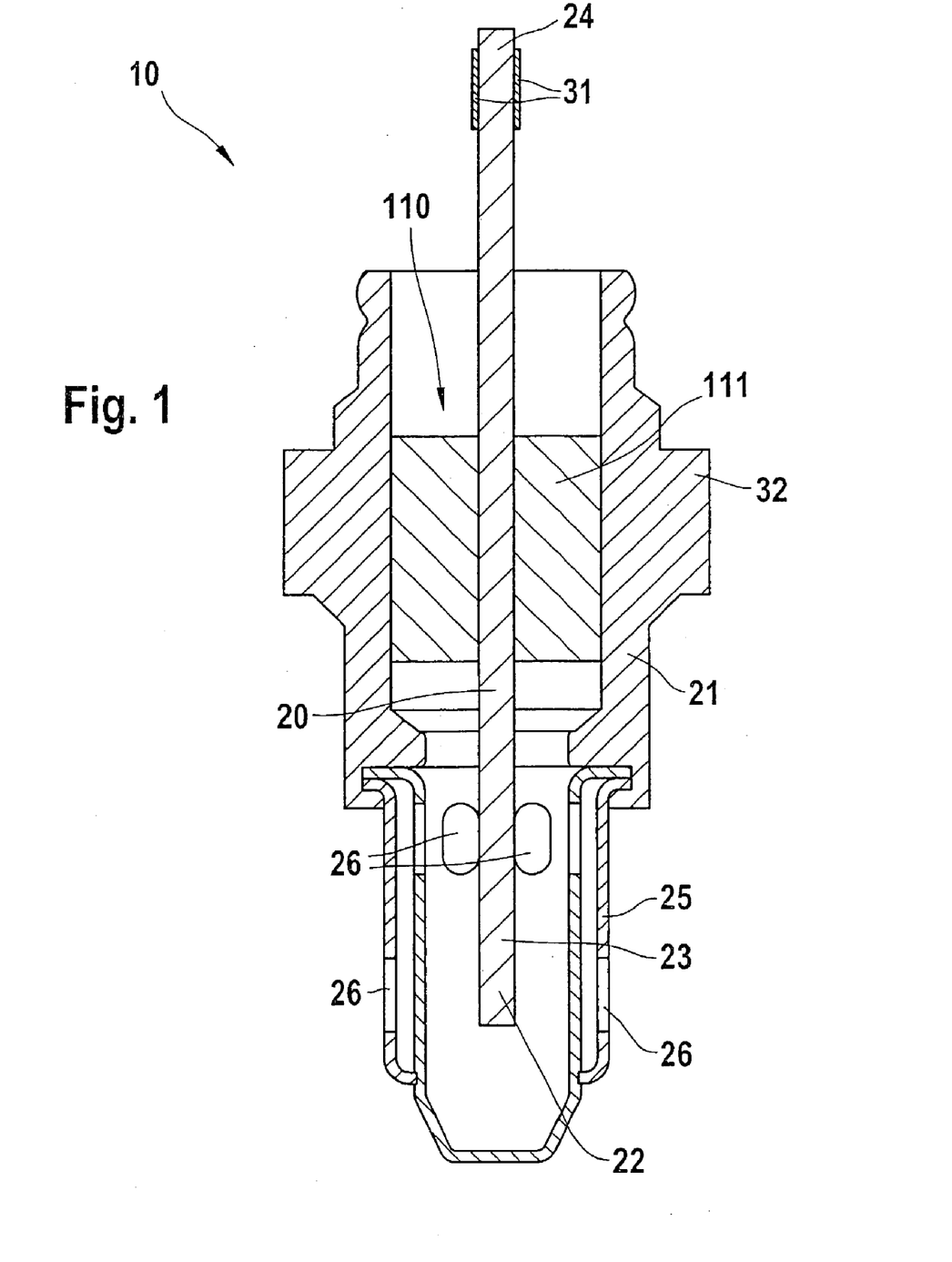
FIG. 1 illustrates a cross-section of a part of a gas sensor according to an example embodiment of the present invention, having a seal assembly.

As a first exemplary embodiment, FIG. 1 shows a part of a gas sensor 10, e.g. an electrochemical sensor for determining the oxygen concentration in an exhaust gas of an internal combustion engine, or for determining the temperature of the exhaust gas of an engine. Gas sensor 10 includes a planar sensor element 20 arranged in a housing 21. Sensor element 20 has a section 23 on the side of the gas to be analyzed and a terminal-side section 24.

At terminal-side section 24 of sensor element 20, contact surfaces 31, which are electrically connected to a measuring element 23 provided at measuring-gas-side section 22 of sensor-element 20, are mounted to the outer surfaces of sensor element 20. A contacting device not shown contacts contact surfaces 31, the contacting device electrically connecting measuring element 23 to an evaluation circuit arranged outside the gas sensor, via a connector cable likewise not shown.

Fastened to the housing on the side facing measuring-gas-side section 23 of sensor element 20 is a double-walled, protective tube 25, which has gas-access openings 26 that allow the measuring gas to access measuring-gas-side section 22 of sensor element 20.

Gas sensor 10 is arranged in an exhaust-pipe measuring opening not shown, and measuring-gas-side region 23 of sensor element 20 and protective tube 25 project into the exhaust pipe. A female screw or screw cap, which acts upon a collar 32 and engages with a thread of the measuring opening of the exhaust pipe, is provided for attaching the gas sensor.

A seal assembly 110 having a sealing element 111 is provided for sealing and supporting sensor element 20 in housing 21. "Under seal assembly 110" is to be understood as a predefined region along the major axis of sensor element 20, as well as along the inner wall of housing 21. Along this predefined region, sealing element 111 completely fills up the space between sensor element 20 and housing 21. The sealing element has a continuous material connection to sensor element 20 and housing 21.

FIGS. 2, 3, 4a, 4b, 5, and 6 illustrate a partial section of the gas sensor represented in FIG. 1. Represented are different example embodiments of the seal assembly 120, 130, 140, 150, 160 and schematics of housing 21 and sensor element 20 in the region of the seal assembly. The housing and the sensor element are designated by the same reference characters as in FIG. 1.

Figure 2:
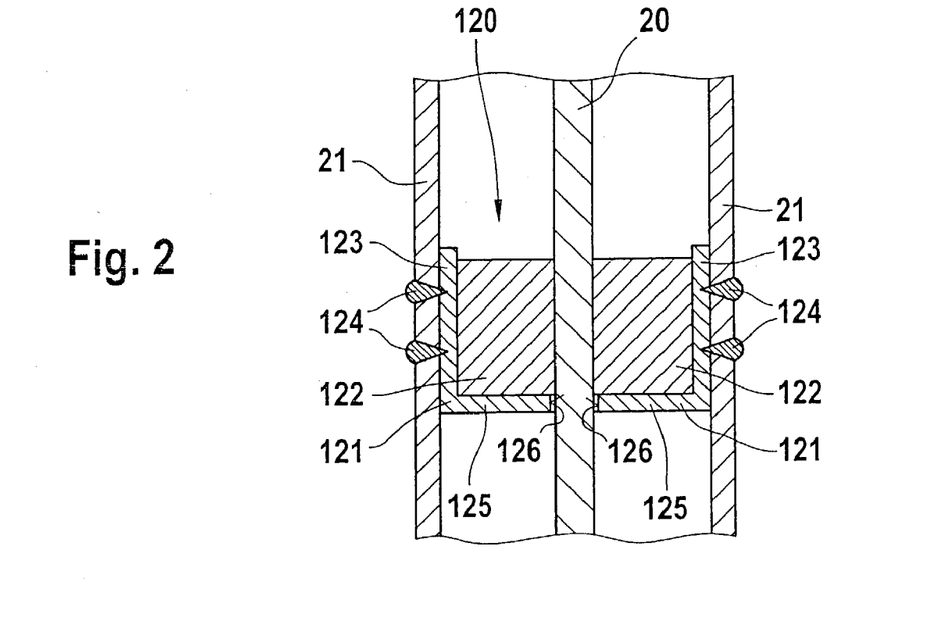
FIG. 2 illustrates schematically a seal assembly including a metallic part and a sealing element.

Seal assembly 120 represented in FIG. 2 includes a machined, metallic part 121 and a sealing element 122. Machined part 121 is shaped similarly to a cup and has a side wall 123 and a base 125. Side wall 123 has a circular cross-section corresponding to the shape of housing 21 and forms a hollow cylinder. Machined, metallic part 121 is closed on at least one end by a base 125. Base 125 is planar in accordance with the base of a pot. Base 125 may also be configured to have a different shape that is tapered with respect to side wall 123, e.g. hemispherical or conical. Base 125 of machined part 121 has a central opening 126 for receiving sensor element 20. In this context, sensor element 20 is arranged on the axis of symmetry of hollow cylindrical side wall 123 of machined part 121. The region between sensor element 20 and machined part 121 is filled in by a sealing element 122. Sealing element 122 may also be provided in the region of opening 126 of machined part 121. Side wall 123 of machined part 121 rests against the inner wall of housing 21, and the machined part may be connected to housing 21 by one or more welded connections 124 (e.g. using laser welding).

Figure 3:
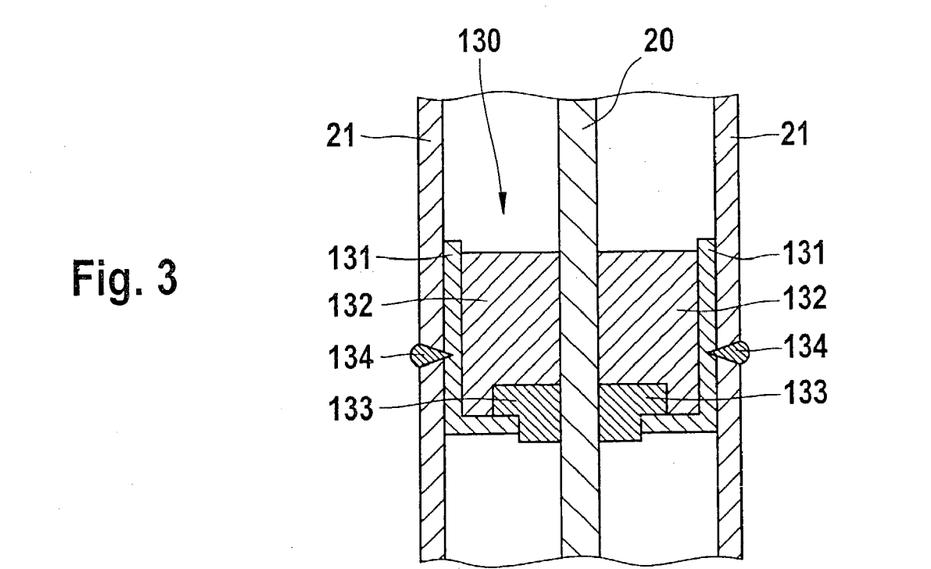
FIG. 3 illustrates schematically a seal assembly according to FIG. 2 including an insulating element.

A modification of the seal assembly according to FIG. 2 is represented in FIG. 3. Seal assembly 130 again includes a machined part 131, which is shaped similarly to a cup, is filled by a sealing element 132, and has a side wall and a base. The side wall is joined to housing 21 by welded connections 134. The base has a central opening, in which an insulating element 133 made out of, for example, a ceramic material is provided. The insulating element has, in turn, a central opening for receiving sensor element 20. On its one side, insulating element 133 is wider than the base opening of machined part 131, so that it may rest on the base of machined part 131.

Figure 4A:
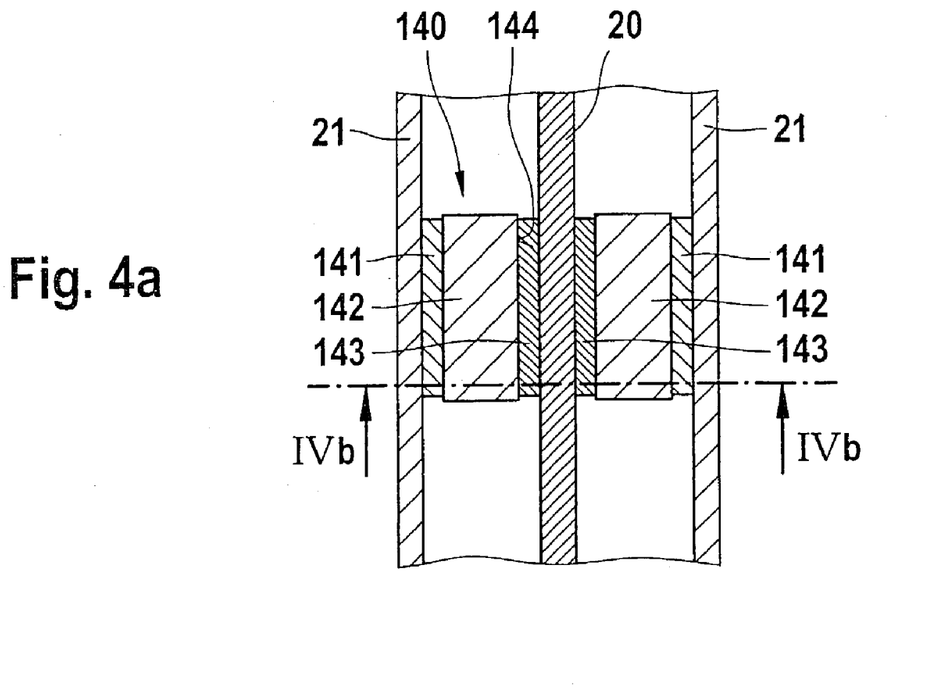
FIG. 4a illustrates schematically a seal assembly including first and second sealing elements.
Figure 4B:
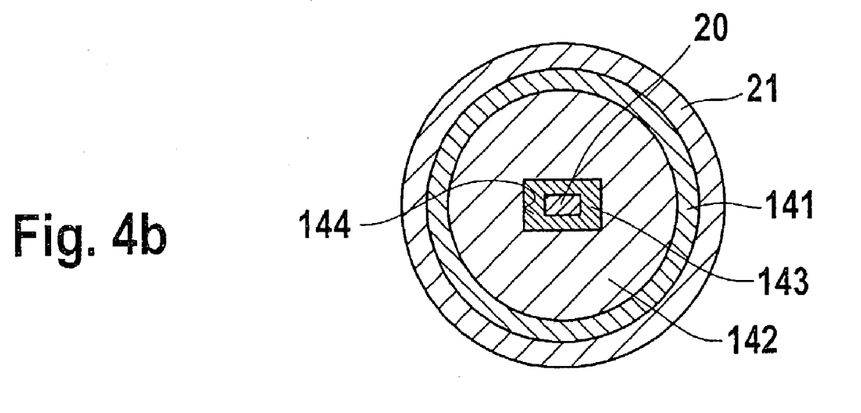
FIG. 4b is a sectional view of the seal assembly according to FIG. 4a along line IVa-IVb.

FIGS. 4a and 4b represent a further modification of the seal assembly, FIG. 4b being a sectional view of seal assembly 140 along line IVb-IVb in FIG. 4a. Seal assembly 140 includes a first sealing element 141, a hollow cylindrical body 142, and a second sealing element 143. The interior of body 142 forms an opening 144 for receiving sensor element 20 and second sealing element 143. Body 142 contains, for example, a ceramic and/or a metallic material. The dimensions of body 142 are selected so that it may be spaced apart from housing 21 and sensor element 20. First sealing element 141 is provided in the gap between body 142 and housing 21, and second sealing element 143 is provided in the gap between body 142 and sensor element 20. Opening 144 of body 142 is shaped so that its cross-section (in the plane perpendicular to the major axis of sensor element 20) corresponds to the correspondingly enlarged cross-section of sensor element 20.

Figure 5:
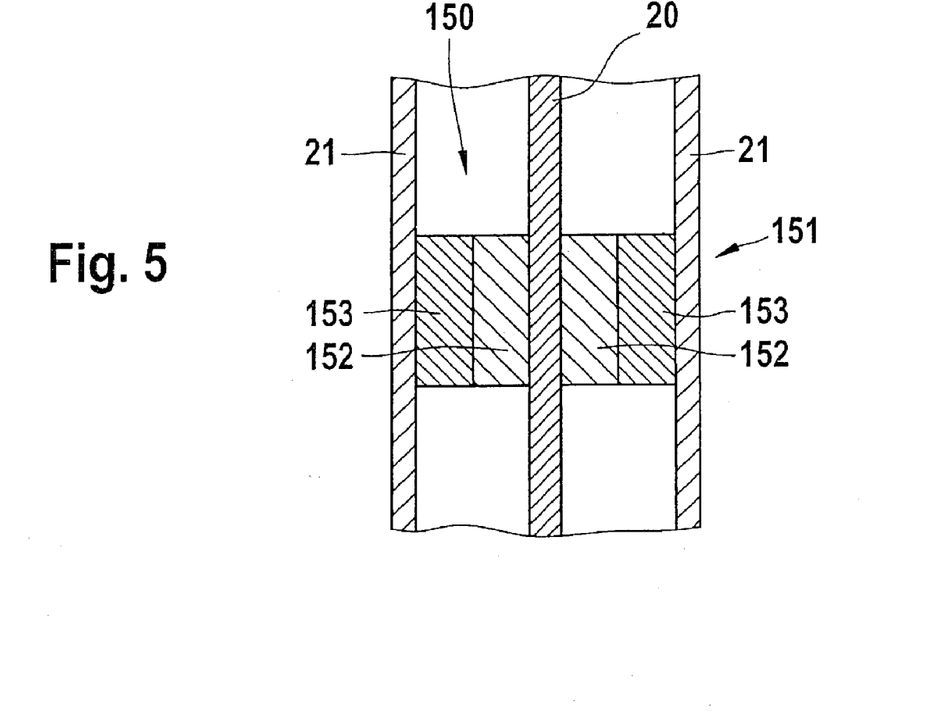
FIG. 5 illustrates schematically a seal assembly including a first region and a second region.

Displayed in FIG. 5 is a example modification of the seal assembly, which differs from the seal assembly according to FIG. 1 in that sealing element 151 has a first region 152 and a second region 153. First region 152 of sealing element 151 surrounds sensor element 20. Second region 153 of sealing element 151 is provided between first region 152 and housing 21. Consequently, the first region is in contact with sensor element 20, and the second region is in contact with housing 21. First region 152 of sealing element 151 has, as a main component, a ceramic material that forms a continuous material connection to the ceramic sensor element. However, second region 153 of the sensor element includes, as a main component, a metallic material that forms a continuous material connection to metallic housing 21. Sealing element 151 may alternatively have a high metallic fraction adjacent to housing 21 and a high ceramic fraction adjacent to sensor element 20, the metallic fraction of sealing element 151 decreasing in steps, or continuously, from housing 21 to sensor element 20, and the ceramic fraction of sealing element 151 increasing in steps, or continuously, from housing 21 to sensor element 20.

Figure 6:
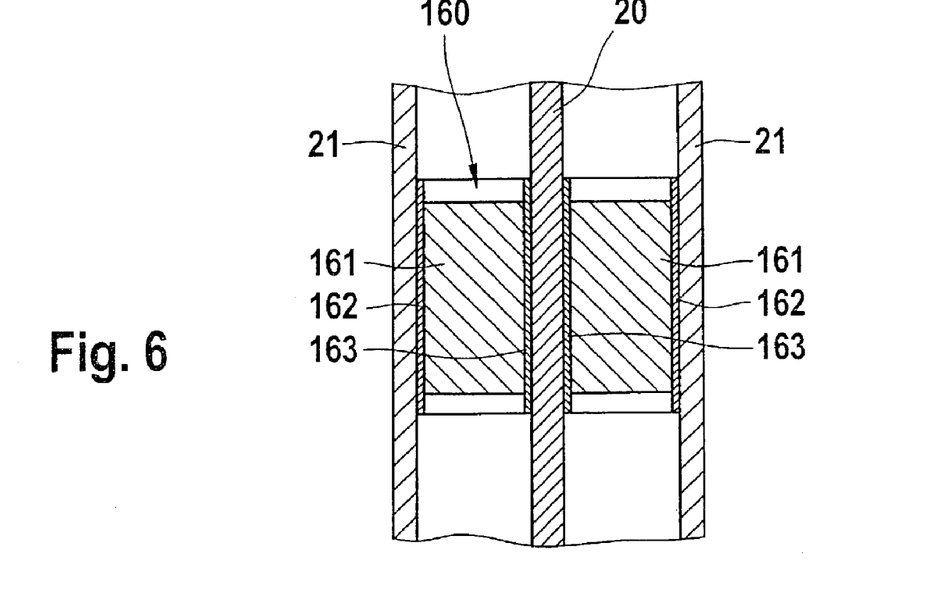
FIG. 6 illustrates schematically a seal assembly including first and/or second layers.

Shown in FIG. 6 is a further example modification of the seal assembly, which differs from the seal assembly according to FIG. 1 in that a first layer 162 is provided between sealing element 161 and housing 21, and/or a second layer 163 is provided between sealing element 161 and sensor element 20. First and second layers 162, 163 may contain, for example, glass or ceramic material and are used for insulating and improving adhesion. In a further example embodiment of the present invention, first layer 162 is configured as an intermediate layer, includes aluminum oxide and/or zirconium oxide and/or aluminum phosphate, and has a thickness of 50 to 200 μm, such as, for example, 100 μm. An intermediate layer may alternatively be provided between sealing element 122, 132, 141, 143 and another metallic element 121, 131, 142 of gas sensor 10. This intermediate layer 162 may prevent cracks from forming in the sealing element during the heat treatment as a result of a reaction of the ceramic material with the metallic material of the housing.

According to an example embodiment of the present invention, sealing elements 111, 122, 132, 141, 143, 151, 161 of seal assemblies 110, 120, 130, 140, 150, 160 represented in FIGS. 1 through 6 contain a ceramic material at a level of 80 to 100 weight percent and a glass fraction of 0 to 20 weight percent. If a particularly good insulation between the sensor element and housing (greater than or equal to 1 MΩ) is required for the operation of sensor element 20, then a glass fraction of less than 3 weight percent may be desired. According to another example embodiment of the present invention, sealing elements 111, 122, 132, 141, 143, 151, 161 include a metallic material at a level of 30 to 100 weight percent, such as, for example, 60 weight percent, and a ceramic material at a level of 0 to 70 weight percent, such as, for example, 40 weight percent.

The starting material of sealing element 111, 122, 132, 141, 143, 151, 161 is subjected to a heat treatment, during which sealing element 111, 122, 132, 141, 143, 151, 161 forms. The heat treatment may cause the volume of sealing element 111, 122, 132, 141, 143, 151, 161 to decrease by a maximum of 5 percent, or even to increase. In this case, the volume of the starting material of sealing element 111, 122, 132, 141, 143, 151, 161 prior to the heat treatment is to be compared to the volume of sealing element 111, 122, 132, 141, 143, 151, 161 after the heat treatment.

During the heat treatment, sealing element 111, 122, 132, 141, 143, 151, 161 may develop a closed porosity with a pore fraction in the range of 15 to 50 volume percent, in particular 35 volume percent. The average pore size of sealing element 111, 122, 132, 141, 143, 151, 161 may lie in the range of 20 to 40 μm, such as, for example, 30 μm. Over 90 percent of the pores may have a pore size in the range of 10 to 60 μm.

In the case of a sealing element that is mainly ceramic, a ceramic material having a coefficient of thermal expansion $\alpha > 7 \cdot 10^{-6}/K$ and a resistivity of $>10^{10}$ Ohm may be selected.

The starting material of sealing element 111, 122, 132, 141, 143, 151, 161 may be inserted into housing 21 as a preformed element. To this end, sealing element 111, 122, 132, 141, 143, 151, 161 may initially be positioned on sensor element 20, and sealing element 111, 122, 132, 141, 143, 151, 161 and sensor element 20 may then be inserted into housing 21 as a unit. In another example method for manufacturing the gas sensor, sensor element 20 is positioned inside housing 21, and the starting material of sealing element 111, 122, 132, 141, 143, 151, 161 is introduced by an injection-molding process.

In the case of the exemplary embodiments of the present invention represented in FIGS. 2 and 3, the heat treatment of sealing element 122, 132 may also be performed outside of the housing. To this end, sensor element 20 and sealing element 122, 132 and, if applicable, insulating element 133 are to be initially introduced into machined, metallic part 121, 131, and the above-mentioned elements are to be subsequently subjected to the heat treatment. Due to the heat treatment, the named elements join to form a unit, which may be inserted into housing 20. Subsequently, machined, metallic part 121, 131 may be joined to housing 20 in a gas-tight manner, by welding (e.g. laser welding or resistance welding, etc.) or soldering, etc.

In the exemplary embodiment according to FIG. 4, sensor element 20, body 142, second sealing element 143, and, if applicable, first sealing element 141 are subjected to a heat treatment outside of housing 20. The unit formed from the named elements by the heat treatment is then to be installed in housing 20. Using, for example, welding (e.g. laser welding, resistance welding, etc.), soldering, etc., housing 20 may be joined in a gas-tight manner to the one first sealing element 141 having a high metallic fraction. As a variant, first sealing element 141 may initially be subjected to a heat treatment in housing 20, which, for example, may occur at a lower temperature than the heat treatment outside of housing 20. The second heat treatment may allow first sealing element 141 to form a gas-tight, integral connection to housing 20 and body 142.

What is claimed is:

1. A gas sensor, comprising:
   a housing;
   a sensor element; and
   a seal assembly arranged to fix the sensor element in the housing and including at least one sealing element;
   wherein the at least one sealing element includes a foam-like structure, the foam-like structure formed of a starting mixture including powdered ceramic powder particles and metal powder particles, the foam-like structure formable by a heat treatment of the starting mixture, a closed porosity formed during the heat treatment by the formation of oxide shells about the metal powder particles and of molten metal within the oxide shells and by flowing out of the molten metal into the ceramic material.

2. The gas sensor according to claim 1, wherein the gas sensor is configured to determine at least one physical quantity of a gas.

3. The gas sensor according to claim 2, wherein the gas includes an exhaust gas of an internal combustion engine.

4. The gas sensor according to claim 1, wherein a ceramic fraction of the sealing element is in the range of 0 to 70 weight percent, and the sealing element includes a metallic component at a level in a range of 30 to 100 weight percent.

5. The gas sensor according to claim 4, wherein the ceramic fraction of the sealing element is 30 weight percent.

6. The gas sensor according to claim 4, wherein the metallic component is at the level of 30 weight percent.

7. The gas sensor according to claim 1, further comprising another metallic element, the sealing element coupled to one of the housing and the another metallic element of the gas sensor by a weld.

8. The gas sensor according to claim 7, wherein the weld includes a laser weld.

9. The gas sensor according to claim 1, wherein the sealing element includes a maximum glass fraction of 20 weight percent.

10. The gas sensor according to claim 1, wherein the sealing element includes a maximum glass fraction of 10 weight percent.

11. The gas sensor according to claim 1, wherein the sealing element is integrally connected to at least one part of the gas sensor adjacent to the sealing element.

12. The gas sensor according to claim 1, wherein the sealing element is integrally connected to at least one of the sensor element and the housing adjacent to the sealing element.

13. The gas sensor according to claim 1, wherein the sealing element completely fills a region between the sensor element and the housing.

14. The gas sensor according to claim 1, wherein the housing is metallic and the seal assembly includes a machined, metallic part joined to the housing by a weld.

15. The gas sensor according to claim 14, wherein the weld includes a laser weld.

16. The gas sensor according to claim 14, wherein the machined, metallic part is cup-shaped, and the sensor element is arranged in a center of the machined, metallic part.

17. The gas sensor according to claim 16, further comprising an insulating element having an opening arranged to receive the sensor element, on one side, the metallic machined part has an opening arranged to receive the insulating element.

18. The gas sensor according to claim 1, wherein the seal assembly includes a body surrounding the sensor element, at least one of a first sealing element arranged between the body and the housing and a second sealing element arranged between the body and the sensor.

19. The gas sensor according to claim 18, wherein, in a sectional plane perpendicular to the sensor element, the body includes an opening arranged to accommodate the sensor element, a shape of the opening corresponding to a cross-section of the sensor element.

20. The gas sensor according to claim 1, wherein the sealing element includes a first region adjacent to the sensor element and a second region adjacent to the housing having a higher metallic fraction and a lower ceramic fraction than the first region, at least one of the metallic and ceramic fraction changing one of in at least one step and continuously from the second region to the first region.

21. The gas sensor according to claim 1, further comprising a layer covering at least one region of at least one of the sealing element, the housing, and the sensor element, the layer including at least one of a ceramic material and a glass.

22. The gas sensor according to claim 1, further comprising an intermediate layer including at least one of aluminum oxide, zirconium oxide, and aluminum phosphate between the sealing element and one of the housing and another metallic element of the gas sensor.

23. A gas sensor, comprising:

a housing;

a sensor element; and a seal assembly arranged to fix the sensor element in the housing and including at least one sealing element;

wherein the sealing element includes a ceramic material sintered in a heat treatment, the sealing element having a closed porosity, a pore fraction of the sealing element in a range of 15 to 50 volume percent, an average pore size in a range of 1 to 100 μm, and at least 90 percent of the pores having a pore size in a range of 10 to 60 μm.

24. The gas sensor according to claim 23, wherein the pore fraction is 35 volume percent.

25. The gas sensor according to claim 23, wherein the average pore size is 30 μm.

\* \* \* \* \*